US006380239B1

(12) United States Patent
Muller et al.

(10) Patent No.: US 6,380,239 B1
(45) Date of Patent: Apr. 30, 2002

(54) SUBSTITUTED 1-OXO- AND 1,3-DIOXOISOINDOLINE AND METHOD OF REDUCING INFLAMMATORY CYTOKINE LEVELS

(75) Inventors: George W. Muller, Bridgewater; David Stirling, Branchburg, both of NJ (US)

(73) Assignee: Celgene Corporation, Warren, NJ (US)

( * ) Notice: Subject to any disclaimer, the term of this patent is extended or adjusted under 35 U.S.C. 154(b) by 0 days.

(21) Appl. No.: 09/528,785

(22) Filed: Mar. 17, 2000

Related U.S. Application Data

(60) Provisional application No. 60/124,942, filed on Mar. 18, 1999.

(51) Int. Cl.$^7$ .................. C07D 209/48; A61K 31/4035; A61F 19/02
(52) U.S. Cl. ........................................ 514/417; 548/479
(58) Field of Search ........................... 548/479; 514/417

(56) References Cited

U.S. PATENT DOCUMENTS

| 5,593,990 A | 1/1997 | D'Amato |
| 5,629,327 A | 5/1997 | D'Amato |
| 5,635,517 A | 6/1997 | Muller et al. |
| 5,712,291 A | 1/1998 | D'Amato |
| 5,798,368 A | 8/1998 | Muller et al. |
| 6,071,948 A | 6/2000 | D'Amato |

FOREIGN PATENT DOCUMENTS

| WO | WO 94/20085 | 9/1994 |
| WO | WO 98/03502 | 1/1998 |
| WO | WO 98/19649 | 5/1998 |
| WO | WO 98/54170 | 12/1998 |

OTHER PUBLICATIONS

Marriott, et. al., "Thalidomide as an Emerging Immunotherapeutic Agent" Trends Immunology Today vol. 20 No. 12, (1999) 538–40.
Muller, et. al., "Amino–Substituted Thalidomide Analogs: Potent Inhibitors of TNF–x Production" Bioorganic & Medicinal Chemistry Letters 9 (1999) 1625–1630.
Corral, et al., "Differential Cytokine Modulation and T Cell Activation by Two Distinct Classes of Thalidomide Analogues That Are Portent Inhibitors of TNF–$\chi^1$" The Journal of Immunology (1999) 163:380–386.
Corral, et. al. "Immunomodulation by Thalidomide and Thalidomide Analogues"; Annals of the Rheumatic Diseases, (1999), vol. 58, Suppl 1, pp 1107–1113.
Valorie, Anne Marie, "Thalidomide; A New Beginning" Cancer Practice (Mar./Apr. 2000), vol. 8, No. 2 P. 101–03.
Smith, R.L. et. al., "Studies on the Relationship between the Chemical Structure and Embryotoxic Acitivity of Thalidomide and Related Compounds" Symp. Embryopathic Act. Drugs (1965) p 194–209.
Quilitz, Rod, "Thalidomide in Oncology: The Peril and The Promise" Oncology Pharmacotherapy (1999) vol. 6, No. 5 483–495.

Kotoh, et. al., "Antiangiogenic Therapy of Human Esophageal Cancers with Thalidomide in Nude Mice" Sugery (1999) vol. 125, No. 5 pp536–544.
Craig et. al. "Potential AntiCancer Agents: 2 Phthalimidoaldehydes and Derivatives" J. Med Chem (1967) vol. 10 pp 1071–1073.
Zwingenberger, et. al., "Immunomodulation by Thalidomide: Systematic Review of the Literature and of Unpublished Observations" Journal of Inflammation 46:177–211 (1996).
Murphy, et. al. Synthesis and Anticancer Activity of Asparagine Analogs; Journal of Pharmaceutical Sciences vol. 69, No. 5, (1980) 553–555.
Caswell, et al. Nitrophthaloyl and Aminophthaloyl Derivatives of Amino Acids; Journal of Chemical and Engineering Data vol. 13, No. 2, (1968) 291–292.
Koch, et. al., "Thalidomide and Congeners as Anti–inflammatory Agents" Progress in Medicinal Chemistry—vol. 22, No. 4 (1985) P165–242.
Tseng, et al. "Rediscovering Thalidomide: A review of its Mechanism of Action, Side Effects, and potential Uses" Journal of American Academy of Dermatology (1996) 35(6):969–979.
Shannon, et. al. "Hydrolysis of Thalidomide abrogates its Ability to Enhance Mononuclear Cell Synthesis of IL–2 as well as its Ability to Suppress the Synthesis of TNF–$\chi$"; Immunopharmacology 36 (1997) 9–15.
Kenyon, et al. "Effects of Thalidomide and Related metabolites in a Mouse Cornela Model of Neovascularization"; Exp. Eye Res. (1997) 64, 971–978.
Miwayama, et al., "Potent Inhibition of Tumor Necrosis Factor–$\chi$ Production by Tetraflourothalidomide and Tetrafluorophthalimides"; J. Med. Chem. (1996), 39, 3044–3045.
Nishimura, et al., "(S)–Form of $\chi$–Methyl–N ($\chi$)–Phthalimidoglutarimide, But Not its (R)–Form, Enhanced Phorbol Ester–Induced Tumor Necrosis Factor–$\chi$ Production By Human Leukemia Cell HL–60: Implication of Optical Resolution of Thalidomidal Effects"; Chem Pharm. Bull. 42(5) 1157–1159 (1994).
Verheul, et al., "Combination Oral Antiangiogenic Therapy with Thalidomide and Sulindac Inhibits Tumour Growth in Rabbits"; British Journal of Cancer (199) 79(1), 114–118.
D'Amato, et al., "Thalidomide is an inhibitor of Angiogenesis"; Proc. Natl. Acad. Sci. USA vol. 91: 4082–4085, (1994).
Shah, et. al., "Synthesis and Enantiomeric Separation of 2–Phthalimidino–glutaric Acid Analogues: Potent Inhibitors of Tumor Metastasis"; J. Med. Chem. (199), 42, 3014–3017.
Udagawa, et al., "Thalidomic and Analogs"; IN *Antioangiogenic Agents Cancer Therapy* (1999) pp 263–274. (ed. B.A. Teicher) (Humana Press Inc., Totowa NJ).

Primary Examiner—Robert W. Ramsuer
Assistant Examiner—Joseph Murray
(74) Attorney, Agent, or Firm—Brian L. Buckwalter; Mathews, Collins, Shepherd & McKay, P.A.

(57) ABSTRACT

1-Oxo- and 1,3-dioxoisoindolines substituted in the 4- or 5-position of the indoline ring reduce the levels of inflammatory cytokines such as TNFα in a mammal. A typical embodiment is 4-(4-amino-1,3-dioxoisoindolin-2-yl)-4-carbamoylbutanoic acid.

18 Claims, No Drawings

SUBSTITUTED 1-OXO- AND 1,3-DIOXOISOINDOLINE AND METHOD OF REDUCING INFLAMMATORY CYTOKINE LEVELS

The present invention claims priority from U.S. Provisional Application, Ser. No. 60/124,942, filed Mar. 18, 1999.

FIELD OF THE INVENTION

The present invention relates to 1-oxo- and 1,3-dioxoisoindolines substituted in the 4- or 5-position of the isoindoline ring, the method of reducing levels of inflammatory cytokines such as tumor necrosis factor-α and treating inflammatory diseases, autoimmune diseases, tumors, and cancers in a mammal through the administration thereof, and to pharmaceutical compositions of such derivatives.

BACKGROUND OF THE INVENTION

Tumor necrosis factor-α (TNFα) is a cytokine which is released primarily by mononuclear phagocytes in response to a number of immunostimulators. It is a key cytokine in the inflammation cascade causing the production and/or release of other cytokines and agents. When administered to animals or humans, it causes inflammation, fever, cardiovascular effects, hemorrhage, coagulation, and phase responses similar to those seen during acute infections and shock states. Excessive or unregulated TNFα production thus has been implicated in a number of disease conditions such as alloreactions such as graft-versus-host disease (GVHD), demyelinating diseases, hypotension, hypertriglyceridaemia, diabetes, osteolysis, neoplasia, leukemia, osteomyelitis, pancreatitis, thrombotic disease, inflammatory bowel disease, scleroderma, rheumatoid arthritis, osteoarthritis, and vasculitis. Anti-TNFα treatments have validated TNFα inhibition in rheumatoid arthritis, inflammatory bowel diseases, endotoxemia and toxic shock syndrome {Tracey et al., Nature 330, 662–664 (1987) and Hinshaw et al., Circ. Shock 30, 279–292 (1990)}; cachexia {Dezube et al., Lancet, 335 (8690), 662 (1990)} and Adult Respiratory Distress Syndrome (ARDS) where TNFα concentration in excess of 12,000 pg/mL have been detected in pulmonary aspirates from ARDS patients {Millar et al., Lancet 2(8665), 712–714 (1989)}. Systemic infusion of recombinant TNFα also resulted in changes typically seen in ARDS {Ferrai-Baliviera et al., Arch. Surg. 124(12), 1400–1405 (1989)}. TNFα appears to be involved in bone resorption diseases, including arthritis. When activated, leukocytes will produce bone-resorption, an activity to which the data suggest TNFα contributes. {Bertolini et al., Nature 319, 516–518 (1986) and Johnson et al., Endocrinology 124(3), 1424–1427 (1989).} TNFα also has been shown to stimulate bone resorption and inhibit bone formation in vitro and in vivo through stimulation of osteoclast formation and activation combined with inhibition of osteoblast function. In Graft versus Host Reaction, increased serum TNFα levels have been associated with major complication following acute allogenic bone marrow transplants {Holler et al., Blood, 75(4), 1011–1016 (1990)}.

Parasitic infections can be controlled by TNFα like malaria or Legionella infection. Cerebral malaria is a lethal hyperacute neurological syndrome associated with high blood levels of TNFα and the most severe complication occurring in malaria patients. Levels of serum TNFα correlated directly with the severity of disease and the prognosis in patients with acute malaria attacks {Grau et al., N. Engl. J. Med. 320(24), 1586–1591 (1989)}.

Angiogenesis, the process of new blood vessel development and formation, plays an important role in numerous physiological events, both normal and pathological. Angiogenesis occurs in response to specific signals and involves a complex process characterized by infiltration of the basal lamina by vascular endothelial cells in response to angiogenic growth signal(s), migration of the endothelial cells toward the source of the signal(s), and subsequent proliferation and formation of the capillary tube. Blood flow through the newly formed capillary is initiated after the endothelial cells come into contact and connect with a preexisting capillary.

Macrophage-induced angiogenesis is known to be mediated by TNFα. Leibovich et al. {Nature, 329, 630–632 (1987)} showed TNFα induces in vivo capillary blood vessel formation in the rat cornea and the developing chick chorioallantoic membranes at very low doses and suggested that TNFα is a candidate for inducing angiogenesis in inflammation, wound repair, and tumor growth. TNFα production also has been associated with cancerous conditions such as tumor lysis syndrome, reoccurrence of bladder cancer, and particularly induced tumors {Ching et al., Brit. J. Cancer, (1955) 72, 339–343, and Koch, Progress in Medicinal Chemistry, 22, 166–242 (1985)}.

The naturally occurring balance between endogenous stimulators and inhibitors of angiogenesis is one in which inhibitory influences predominate. Rastinejad et al., 1989, Cell 56:345–355. In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail.

Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., 1991, Biotech. 9:630–634; Folkman et al., 1995, N. Engl. J. Med., 333:1757–1763; Auerbach et al., 1985, J. Microvasc. Res. 29:401–411; Folkman, 1985, Advances in Cancer Research, eds. Klein and Weinhouse, Academic Press, New York, pp. 175–203; Patz, 1982, Am. J. Opthalmol. 94:715–743; and Folkman et al., 1983, Science 221:719–725. In a number of pathological conditions, the process of angiogenesis contributes to the disease state. For example, significant data have accumulated which suggest that the growth of solid tumors is dependent on angiogenesis. Folkman and Klagsbrun, 1987, Science 235:442–447.

The maintenance of the avascularity of the cornea, lens, and trabecular meshwork is crucial for vision as well as to ocular physiology. See, e.g., reviews by Waltman et al., 1978, Am. J. Ophthal. 85:704–710 and Gartner et al., 1978, Surv. Ophthal. 22:291–312. Currently, the treatment of these diseases, especially once neovascularization has occurred, is inadequate and blindness often results.

An inhibitor of angiogenesis could have an important therapeutic role in limiting the contributions of this process to pathological progression of the underlying disease states as well as providing a valuable means of studying their etiology. For example, agents that inhibit tumor neovascularization could play an important role in inhibiting metastatic tumor growth.

The components of angiogenesis relating to vascular endothelial cell proliferation, migration and invasion, have been found to be regulated in part by polypeptide growth factors. Experiments in culture, indicate that endothelial cells exposed to a medium containing suitable growth factors can be induced to evoke some or all of the angiogenic responses. Several polypeptides with in vitro endothelial growth promoting activity have been identified. Examples include acidic and basic fibroblast growth factors, transforming growth factors α and β, platelet-derived endothelial cell growth factor, granulocyte colony-stimulating factor, interleukin-8, hepatocyte growth factor, proliferin, vascular endothelial growth factor and placental growth factor. See, e.g., review by Folkman et al., 1995, *N. Engl. J. Med.*, 333:1757–1763.

Several kinds of compounds have been used to prevent angiogenesis. Taylor et al. have used protamine to inhibit angiogenesis, see Taylor et al., *Nature* 297:307 (1982). The toxicity of protamine limits its practical use as a therapeutic. Folkman et al. have disclosed the use of heparin and steroids to control angiogenesis. See Folkman et al., *Science* 221:719 (1983) and U.S. Pat. Nos. 5,001,116 and 4,994,443. Steroids, such as tetrahydrocortisol, which lack gluco and mineral corticoid activity, have been found to be angiogenic inhibitors. Interferon β is also a potent inhibitor of angiogenesis induced by allogeneic spleen cells. See Sidky et al., *Cancer Research* 47:5155–5161 (1987). Human recombinant alpha interferon-α is reported to be successfully used in the treatment of pulmonary hemangiomatosis, an angiogenesis-induced disease. See White et al., *New England J. Med.* 320:1197–1200 (1989).

Other agents that have been used to inhibit angiogenesis include ascorbic acid ethers and related compounds. See Japanese Kokai Tokkyo Koho No. 58-131978. Sulfated polysaccharide DS 4152 also shows angiogenic inhibition. See Japanese Kokai Tokkyo Koho No. 63-119500. A fungal product, fumagillin, is a potent angiostatic agent in vitro. The compound is toxic in vivo, but a synthetic derivative, AGM 12470, has been used in vivo to treat collagen II arthritis. Fumagillin and O-substituted fumagillin derivatives are disclosed in EPO Publication Nos. 0325199A2 and 0357061A1.

In U.S. Pat. No. 5,874,081, Parish teaches use of monoclonal antibodies to inhibit angiogenesis. In WO92/12717, Brem et al. teach that some tetracyclines, particularly Minocycline, Chlortetracycline, Demeclocycline and Lymecycline are useful as inhibitors of angiogenesis. In Cancer Research 51, 672–675, Jan. 15, 1991, Brem et al. teach that Minocycline inhibits angiogenesis to an extent comparable to that of the combination therapy of heparin and cortisone. In Cancer Research 52, 6702–6704, Dec. 1, 1992, Teicher et al. teach that tumor growth is decreased and the number of metastases is reduced when the anti-angiogenic agent of metastases is reduced when the anti-angiogenic agent Minocycline is used in conjunction with cancer chemotherapy or radiation therapy.

All of the various cell types of the body can be transformed into benign or malignant tumor cells. The most frequent tumor site is lung, followed by colorectal, breast, prostate, bladder, pancreas, and then ovary. Other prevalent types of cancer include leukemia, central nervous system cancers, including brain cancer, melanoma, lymphoma, erythroleukemia, uterine cancer, and head and neck cancer.

Cancer is now primarily treated with one or a combination of three types of therapies: surgery, radiation, and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia. Chemotherapy involves the disruption of cell replication or cell metabolism. It is used most often in the treatment of leukemia, as well as breast, lung, and testicular cancer.

There are five major classes of chemotherapeutic agents currently in use for the treatment of cancer: natural products and their derivatives; anthracyclines; alkylating agents; anti-proliferatives (also called antimetabolites); and hormonal agents.

Chemotherapeutic agents are often referred to as antineoplastic agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Antimetabolites are typically reversible or irreversible enzyme inhibitors, or compounds that otherwise interfere with the replication, translation or transcription of nucleic acids.

Several synthetic nucleosides have been identified that exhibit anticancer activity. A well known nucleoside derivative with strong anticancer activity is 5-fluorouracil. 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381, and in Japanese patent publication Nos. 50-50383, 50-50384, 50-64281, 51-146482, and 53-84981. U.S. Pat. No. 4,000,137 discloses that the peroxidate oxidation product of inosine, adenosine, or cytidine with methanol or ethanol has activity against lymphocytic leukemia.

Cytosine arabinoside (also referred to as Cytarabin, araC, and Cytosar) is a nucleoside analog of deoxycytidine that was first synthesized in 1950 and introduced into clinical medicine in 1963. It is currently an important drug in the treatment of acute myeloid leukemia. It is also active against acute lymphocytic leukemia, and to a lesser extent, is useful in chronic myelocytic leukemia and non-Hodgkin's lymphoma. The primary action of araC is inhibition of nuclear DNA synthesis. Handschumacher, R. and Cheng, Y., "Purine and Pyrimidine Antimetabolites", Cancer Medicine, Chapter XV-1, $3^{rd}$ Edition, Edited by J. Holland, et al., Lea and Febigol, publishers. 5-Azacytidine is a cytidine analog that is primarily used in the treatment of acute myelocytic leukemia and myelodysplastic syndrome.

2-Fluoroadenosine-5'-phosphate (Fludara, also referred to as FaraA)) is one of the most active agents in the treatment of chronic lymphocytic leukemia. The compound acts by inhibiting DNA synthesis. Treatment of cells with F-araA is associated with the accumulation of cells at the G1/S phase boundary and in S phase; thus, it is a cell cycle S phase-specific drug. Incorporation of the active metabolite, F-araATP, retards DNA chain elongation. F-araA is also a potent inhibitor of ribonucleotide reductase, the key enzyme responsible for the formation of dATP. 2-Chlorodeoxyadenosine is useful in the treatment of low grade B-cell neoplasms such as chronic lymphocytic leukemia, non-Hodgkins' lymphoma, and hairy-cell leukemia. The spectrum of activity is similar to that of Fludara. The compound inhibits DNA synthesis in growing cells and inhibits DNA repair in resting cells.

Although a number of chemotherapeutic agents have been identified and are currently used for the treatment of cancer, new agents are sought that are efficacious and which exhibit low toxicity toward healthy cells.

TNFα also plays a role in the area of asthma and other chronic pulmonary inflammatory diseases. The deposition of silica particles leads to silicosis, a disease of progressive respiratory failure caused by a fibrotic reaction. Pretreatment with antibodies to TNFα almost completely blocked the silica-induced lung fibrosis in mice {Pignet et al., Nature, 344, 245–247 (1990)}. High levels of TNFα production (in the serum and in isolated macrophages) have been demonstrated in animal models of silica and asbestos induced fibrosis {Bissonnette et al., Inflammation 13(3), 329–339 (1989)}. Alveolar macrophages from pulmonary sarcoidosis patients have also been found to spontaneously release massive quantities of TNFα as compared with macrophages from normal donors {Baughman et al., J. Lab. Clin. Med. 115(1), 36–42 (1990)}.

TNFα is also implicated in the inflammatory response which follows reperfusion, called reperfusion injury, and is a major cause of tissue damage after loss of blood flow {Vedder et al., PNAS 87, 2643–2646 (1990)}. Tissue damage can also include surgical injury and inflammation, problems following heart transplants, systematic inflammatory response syndrome, and multiple organ dysfunction syndrome. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et al., J. Cell Biol. 107, 1269–1277 (1988)}. TNFα has pro-inflammatory activities that together with its early production (during the initial stage of an inflammatory event) make it a likely mediator of tissue injury in several important disorders including but not limited to, myocardial infarction, stroke and circulatory shock. Of specific importance can be TNFα induced expression of adhesion molecules, such as intercellular adhesion molecule (ICAM) or endothelial leukocyte adhesion molecule (ELAM) on endothelial cells {Munro et al., Am. J. Path. 135(1), 121–132 (1989)}.

TNFα blockage with monoclonal anti-TNFα antibodies has been shown to be beneficial in rheumatoid arthritis {Elliot et al., Int. J. Pharmac. 1995 17(2), 141–145}. High levels of TNFα are associated with Crohn's disease {von Dullemen et al., Gastroenterology, 1995 109(1), 129–135} and clinical benefit has been achieved with TNFα antibody treatment.

Moeller in U.S. Pat. No. 5,231,024, describes hybridoma cell lines which synthesize highly specific monoclonal antibodies (mAb) against human tumor necrosis factor (TNF). Rubin in U.S. Pat. No. 4,870,163, describes hybridomas producing monoclonal antibodies to human tumor necrosis factor. Barbanti in U.S. Pat. No. 5,436,154, suggested that antibodies against TNFα and, possibly, also antibodies against TNFβ could be therapeutically useful in those disease states in which these polypeptides exert a pathogenic effect. In order to be therapeutically useful antibodies against TNFα should be able to neutralize the toxic effects of TNFα in vivo. Polyclonal antibodies are easily obtainable from the serum of hyperimmunized animals. These polyclonal antibody preparations, however, are not optimal for in vivo use because they are a mixture of antibodies containing antibodies which do not neutralize TNFα they are a mixture of antibodies containing different antibodies having different affinities for the same epitope and they are difficult to standardize in terms of potency because of lot-to-lot variations.

Moreover, it is known that TNFα is a potent activator of retrovirus replication including activation of HIV-1. {Duh et al., Proc. Nat. Acad. Sci. 86, 5974–5978 (1989); Poll et al., Proc. Nat. Acad. Sci. 87, 782–785 (1990); Monto et al., Blood 79, 2670 (1990); Clouse et al., J. Immunol. 142, 431–438 (1989); Poll et al., AIDS Res. Hum. Retrovirus, 191–197 (1992)}. AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T-cell activation and such virus protein expression and/or replication is mediated or maintained by such T-cell activation. Once an activated T lymphocyte is infected with HIV, the T lymphocyte must continue to be maintained in an activated state to permit HIV gene expression and/or HIV replication. Cytokines, specifically TNFα are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual assists in limiting the maintenance of T lymphocyte caused by HIV infection.

Monocytes, macrophages, and related cells, such as kupffer and glial cells, also have been implicated in maintenance of the HIV infection. These cells, like T-cells, are targets for viral replication and the level of viral replication is dependent upon the activation state of the cells. {Rosenberg et al., The Immunopathogenesis of HIV Infection, Advances in Immunology, 57 (1989)}. Cytokines, such as TNFα, have been shown to activate HIV replication in monocytes and/or macrophages {Poli et al., Proc. Natl. Acad. Sci., 87, 782–784 (1990)}, therefore, prevention or inhibition of cytokine production or activity aids in limiting HIV progression for T-cells. Additional studies have identified TNFα as a common factor in the activation of HIV in vitro and has provided a clear mechanism of action via a nuclear regulatory protein found in the cytoplasm of cells (Osborn, et al., PNAS 86 2336–2340). This evidence suggests that a reduction of TNFα synthesis can have an antiviral effect in HIV infections, by reducing the transcription and thus virus production.

AIDS viral replication of latent HIV in T-cell and macrophage lines can be induced by TNFα {Folks et al., PNAS 86, 2365–2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., PNAS 86, 2336–2340 (1989)}. TNFα in AIDS associated cachexia is suggested by elevated serum TNFα and high levels of spontaneous TNFα production in peripheral blood monocytes from patients {Wright et al., *J. Immunol.* 141(1), 99–104 (1988)}. TNFα affects microsporidiosis (cause of chronic diarrhea in HIV patients) and oral aphthous ulcers in HIV patients. TNFα has been implicated in various roles with viral infections such as the cytomegalia virus (CMV), influenza virus, adenovirus, and the herpes family of viruses for similar reasons as those noted. Some viruses such as the Sendai virus and influenza induce TNFα.

The nuclear factor κB (NFκB) is a pleiotropic transcriptional activator (Lenardo, et al., *Cell* 1989, 58, 227–29). NFκB has been implicated as a transcriptional activator in a variety of disease and inflammatory states and is thought to regulate cytokine levels including but not limited to TNFα and also to be an activator of HIV transcription (Dbaibo, et al., *J. Biol. Chem.* 1993, 17762–66; Duh et al., *Proc. Natl. Acad. Sci.* 1989, 86, 5974–78; Bachelerie et al., *Nature* 1991, 350, 709–12; Boswas et al., *J. Acquired Immune Deficiency Syndrome* 1993, 6, 778–786; Suzuki et al., *Biochem. And Biophys. Res. Comm.* 1993, 193, 277–83; Suzuki et al., *Biochem. And Biophys. Res Comm.* 1992, 189, 1709–15; Suzuki et al., *Biochem. Mol. Bio. Int.* 1993, 31(4), 693–700; Shakhov et al., *Proc. Natl. Acad. Sci. USA* 1990, 171, 35–47; and Staal et al., *Proc. Natl. Acad. Sci. USA* 1990, 87, 9943–47). Thus, inhibition of NFκB binding can regulate transcription of cytokine gene(s) and through this modulation and other mechanisms be useful in the inhibition of a multitude of disease states. The compounds described herein can inhibit the action of NFκB in the nucleus and thus are useful in the treatment of a variety of diseases including but not limited to rheumatoid arthritis, rheumatoid spondylitis, osteoarthritis, other arthritic conditions, septic shock, septis, endotoxic shock, graft versus host disease, wasting, Crohn's disease, ulcerative colitis, multiple sclerosis, systemic lupus erythrematosis, ENL in leprosy, HIV, AIDS, and opportunistic infections in AIDS. TNFα and NFκB levels are influenced by a reciprocal feedback loop. As noted above, the compounds of the present invention affect the levels of both TNFα and NFκB. Of course, levels refer to activity levels as well as concentration levels or absolute levels.

Many cellular functions are mediated by levels of adenosine 3',5'-cyclic monophosphate (cAMP). Such cellular functions can contribute to inflammatory conditions and diseases including asthma, inflammation, and other conditions (Lowe and Cheng, *Drugs of the Future*, 17(9), 799–807, 1992). It has been shown that the elevation of cAMP in inflammatory leukocytes inhibits their activation and the subsequent release of inflammatory mediators, including TNFα and NFκB. Increased levels of cAMP also leads to the relaxation of airway smooth muscle. Phosphodiesterases control the level of cAMP through hydrolysis and inhibitors of phosphodiesterases have been shown to increase cAMP levels.

Decreasing TNFα levels and/or increasing cAMP levels thus constitutes a valuable therapeutic strategy for the treatment of many inflammatory, infectious, immunological or malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, and alveolar injury. Prior efforts directed to the suppression of the effects of TNFα have ranged from the utilization of steroids such as dexamethasone and prednisolone to the use of both polyclonal and monoclonal antibodies {Beutler et al., *Science* 234, 470–474 (1985); WO 92/11383}.

DETAILED DESCRIPTION

The present invention is based on the discovery that certain classes of non-polypeptide compounds, more fully described herein, decrease the levels of TNFα, increase cAMP levels, inhibit angiogenesis, inhibit tumor growth, and inhibit inflammatory cytokines. The present invention thus relates to 1-oxo-indolines and 1,3-dioxoindolines substituted in the 4-position or 5-position of the isoindoline ring, the method of reducing levels of tumor necrosis factor a and other inflammatory cytokines in a mammal through the administration of such derivatives, and pharmaceutical compositions containing such derivatives. Decreasing TNFα levels and/or increasing cAMP levels and/or inhibiting angiogenesis in vivo, in vitro, and in potable media also constitute valuable therapeutic strategies.

In particular, the invention pertains to (a) a 1,3-dioxoindoline of the formula:

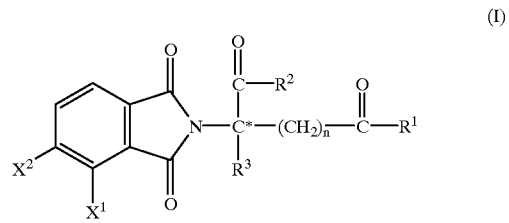

(I)

in which the carbon atom designated C* constitutes a center of chirality (when n is not zero and $R^1$ is not the same as $R^2$); one of $X^1$ and $X^2$ is amino, nitro, alkyl of one to six carbons, or NH—Z, and the other of $X^1$ or $x^2$ is hydrogen; each of $R^1$ and $R^2$ independent of the other, is hydroxy or NH—Z; $R^3$ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if $X^1$ is amino, and n is 1 or 2, then $R^1$ and $R^2$ are not both hydroxy;

(b) the salts of Formula I;

(c) a 1-oxoindoline of the formula:

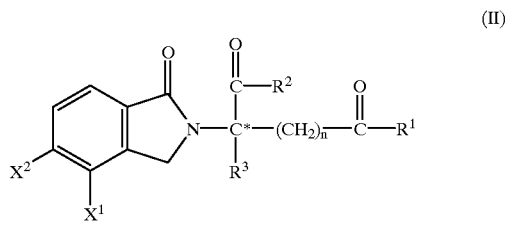

(II)

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl or acyl of one to six carbons; and n has a value of 0, 1, or 2;

(d) the salts of Formula II.

Unless otherwise defined, the term alkyl denotes a univalent saturated branched or straight hydrocarbon chain containing from one to six carbon atoms. Representative of such alkyl groups are methyl, ethyl, propyl, isopropyl, butyl, isobutyl, sec-butyl, and tert-butyl. Alkoxy refers to an alkyl group bound to the remainder of the molecule through an ethereal oxygen atom. Representative of such alkoxy groups are methoxy, ethoxy, propoxy, isopropoxy, butoxy, isobutoxy, sec-butoxy, and tert-butoxy. Halo includes bromo, chloro, fluoro, and iodo.

Salts of Formula I and Formula II include carboxylic acid salts and the acid addition salts of the substituted 1-oxoisoindolines and substituted 1,3-dioxoindolines which contain a nitrogen atom capable of being protonated.

The compounds of Formula I and II are used, under the supervision of qualified professionals, to inhibit the undesirable effects of TNFα and other inflammatory cytokines including IL-1, IL-6, and IL-12 and/or treat undesired angiogenesis and tumor growth. The compounds can be administered orally, rectally, or parenterally, alone or in combination with other therapeutic agents including antibiotics, steroids, chemotherapeutic agents, etc., to a mammal in need of treatment; e.g., in the treatment of cancers, rheumatoid arthritis, inflammatory bowel disease, muscular dystrophy, Crohn's disease, etc.

The compounds of the present invention also can be used topically in the treatment or prophylaxis of disease states mediated or exacerbated by excessive TNFα production or inflammation, respectively, such as viral infections, such as those caused by the herpes viruses, viral conjunctivitis, psoriasis, atopic dermatitis, etc.

The compounds also can be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anemia virus, caprine arthritis virus, visna virus, and maedi virus, as well as other lentiviruses.

The compounds of Formula I are readily prepared through a number of routes. In one embodiment, a glutamic acid, glutamine, isoglutamine, aspartic acid, aspargine, or isoaspargine is allowed to react with a substituted phthalic anhydries such as 1,3-dioxo-isobenzofuran that is further substituted in the 4- or 5-position:

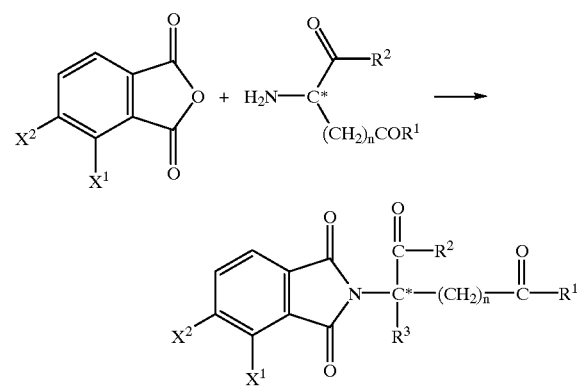

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl of one to six carbons; and n has a value of 0, 1, or 2; provided that if $X^1$ is amino, and n is 1 or 2, then $R^1$ and $R^2$ are other than hydroxy. Substituted N-carbethoxyphthalimides (see Example 1) can be used in place of the anhydride.

In a second embodiment, the following reaction is used to prepare compounds of Formula I:

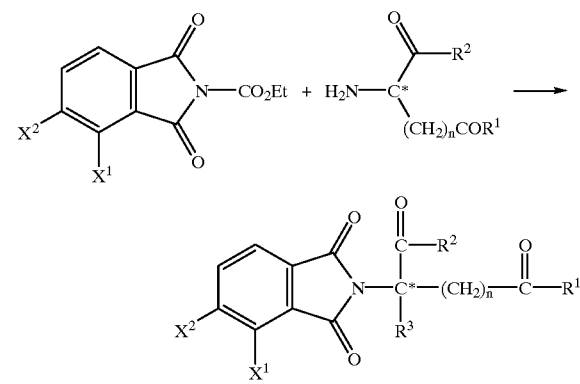

The compounds of Formula II are readily prepared through a number of routes. In a first embodiment, a glutamic acid, glutamine, isoglutamine, aspartic acid, aspargine, or isoaspargine is allowed to react with a tetrasubstituted phenyl:

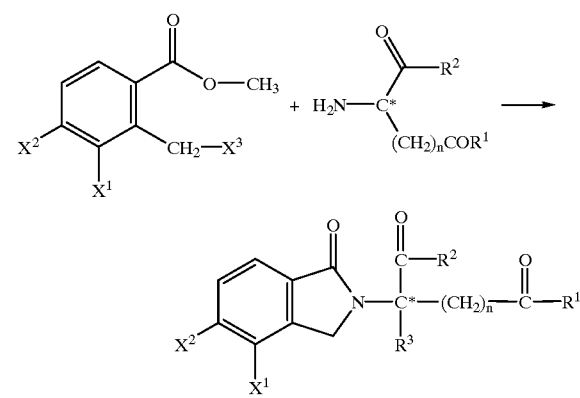

in which the carbon atom designated C* constitutes a center of chirality except when n is zero and $R^1=R^2$; $X^2$ is amino, nitro, alkyl of one to six carbons, or NH—Z; $X^3$ is a halogen; each of $R^1$ and $R^2$ independent of the other, is hydroxy or NH—Z; $R^3$ is alkyl or acyl of one to six carbons, halo, or hydrogen; Z is hydrogen, aryl, or an alkyl of one to six carbons; and n has a value of 0, 1, or 2; provided that if $X^1$ is amino, and n is 1 or 2, then $R^1$ and $R^2$ are not both hydroxy.

In a second embodiment of preparing Formula II, a glutamic acid, glutamine, isoglutamine, aspartic acid, aspargine, or isoaspargine is allowed to react with a phthalic dialdehyde that is substituted in the 3- or 4-position:

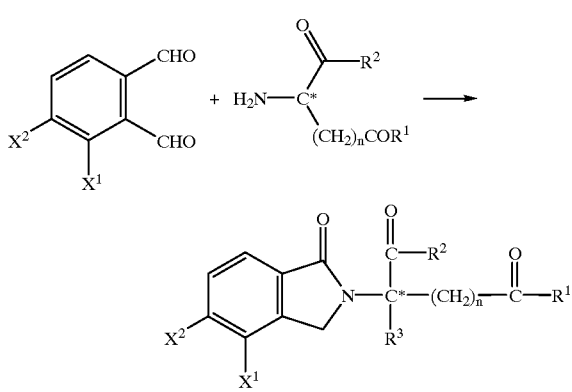

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl or acyl group of one to six carbons; and n has a value of 0, 1, or 2; provided that if $X^1$ is amino, and n is 1 or 2, then $R^1$ and $R^2$ are other than hydroxy.

The carbon atom to which $R^3$ is bound in the compounds of Formula I constitutes a center of chirality when n is not zero and $R^1$ is not the same group as $R^2$, thereby giving rise to optical isomers. Both mixtures of these isomers and the seperated individual isomers themselves, as well as diastereomers when a second chiral center is present, as for example in a branched alkyl substituent of 4 to 6 carbons, are within the scope of the present invention. The racemates can be used as such or can be separated into their individual isomers mechanically as by chromatography using a chiral absorbant. Alternatively, the individual isomers can be prepared stereoselectively or separated chemically from a mixture by forming salts with a chiral acid or base, such as the individual enantiomers of 10-camphorsulfonic acid, camphoric acid, α-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as to obtain either or both substantially free of the other; i.e., in a form having an optical purity of >95%.

The present invention also pertains to the physiologically acceptable non-toxic acid addition salts of the compound of Formula I which contain a group capable of being protonated; e.g., amino. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

Representative examples of compounds included in this invention are: 2-(n-X-1,3-dioxoisoindolin-2-yl)glutaric acid; 2-(n-X-1,3-dioxoisoindolin-2-yl)-4-carbamoylbutanoic acid; 4-(n-X-1,3-dioxoisoindolin-2-yl)-4-carbamoylbutanoic acid; 2-(n-X-1,3-dioxoisoindolin-2-yl)succinic acid; 2-(n-X-1,3-dioxoisoindolin-2-yl)-3-carbamoylpropanoic acid; 3-(n-X-1,3-dioxoisoindolin-2-yl)-3-carbamoylpropanoic acid; 2-(n-X-1-oxoisoindolin-2-yl)glutaric acid; 2-(n-X-1-oxoisoindolin-2-yl)-4-carbamoylbutanoic acid; 4-(n-X-1-oxoisoindolin-2-yl)-4-carbamoylbutanoic acid; 2-(n-X-1-oxoisoindolin-2-yl)succinic acid; 2-(n-X-1-oxoisoindolin-2-yl)-3-carbamoylpropanoic acid; and 3-(n-X-1-oxoisoindolin-2-yl)-3-carbamoylpropanoic acid in which n is 3 or 4, and X is nitro, amino, N-methylamino, methyl, ethyl, propyl, isopropyl, or butyl.

Specific examples include: 2-(3-nitro-1,3-dioxoisoindolin-2-yl)glutatic acid; 2-(3-nitro-1,3-dioxoisoindolin-2-yl)-4-carbamoylbutanoic acid; 4-(3-nitro-1,3-dioxoisoindolin-2-yl)-4-carbamoylbutanoic acid; 2-(3-nitro-1,3-dioxoisoindolin-2-yl)succinic acid; 2-(3-nitro-1,3-dioxoisoindolin-2-yl)-3-carbamoylpropanoic acid; 3-(3-nitro-1,3-dioxoisoindolin-2-yl)-3-carbamoylpropanoic acid; 2-(3-nitro-1-oxoisoindolin-2-yl)glutaric acid; 2-(3-nitro-1-oxoisoindolin-2-yl)-4-carbamoylbutanoic acid; 4-(3-nitro-1-oxoisoindolin-2-yl)-4-carbamoylbutanoic acid; 2-(3-nitro-1-oxoisoindolin-2-yl)succinic acid; 2-(3-nitro-1-oxoisoindolin-2-yl)-3-carbamoylpropanoic acid; 3-(3-nitro-1-oxoisoindolin-2-yl)-3-carbamoylpropanoic acid; 2-(4-nitro-1,3-dioxoisoindolin-2-yl)odipic acid; 2-(4-nitro-1,3-dioxoisoindolin-2-yl)-4-carbamoylbutanoic acid; 4-(4-nitro-1,3-dioxoisoindolin-2-yl)-4-carbamoylbutanoic acid; 2-(4-nitro-1,3-dioxoisoindolin-2-yl)succinic acid; 2-(4-nitro-1,3-dioxoisoindolin-2-yl)-3-carbamoylpropanoic acid; 3-(4-nitro-1,3-dioxoisoindolin-2-yl)-3-carbamoylpropanoic acid; 2-(4-nitro-1-oxoisoindolin-2-yl)glutaric acid; 2-(4-nitro-1-oxoisoindolin-2-yl)-4-carbamoylbutanoic acid; 4-(4-nitro-1-oxoisoindolin-2-yl)-4-carbamoylbutanoic acid; 2-(4-nitro-1-oxoisoindolin-2-yl)succinic acid; 2-(4-nitro-1-oxoisoindolin-2-yl)-3-carbamoylpropanoic acid; 3-(4-nitro-1-oxoisoindolin-2-yl)-3-carbamoylpropanoic acid; 2-(3-amino-1,3-dioxoisoindolin-2-yl)glutaric acid; 2-(3-amino-1,3-dioxoisoindolin-2-yl)-4-carbamoylbutanoic acid; 4-(3-amino-1,3-dioxoisoindolin-2-yl)-4-carbamoylbutanoic acid; 2-(3-amino-1,3-dioxoisoindolin-2-yl)succinic acid; 2-(3-amino-1,3-dioxoisoindolin-2-yl)-3-carbamoylpropanoic acid; 3-(3-amino-1,3-dioxoisoindolin-2-yl)-3-carbamoylpropanoic acid; 2-(3-amino-1-oxoisoindolin-2-yl)glutaric acid; 2-(3-amino-1-oxoisoindolin-2-yl)-4-carbamoylbutanoic acid; 4-(3-amino-1-oxoisoindolin-2-yl)-4-carbamoylbutanoic acid; 2-(3-amino-1-oxoisoindolin-2-yl)succinic acid; 2-(3-amino-1-oxoisoindolin-2-yl)-3-carbamoylpropanoic acid; 3-(3-amino-1-oxoisoindolin-2-yl)-3-carbamoylpropanoic acid; 2-(4-amino-1,3-dioxoisoindolin-2-yl)odipic acid; 2-(4-amino-1,3-dioxoisoindolin-2-yl)-4-carbamoylbutanoic acid; 4-(4-amino-1,3-dioxoisoindolin-2-yl)-4-carbamoylbutanoic acid; 2-(4-amino-1,3-dioxoisoindolin-2-yl)succinic acid; 2-(4-amino-1,3-dioxoisoindolin-2-yl)-3-carbamoylpropanoic acid; 3-(4-amino-1,3-dioxoisoindolin-2-yl)-3-carbamoylpropanoic acid; 2-(4-amino-1-oxoisoindolin-2-yl)glutaric acid; 2-(4-amino-1-oxoisoindolin-2-yl)-4-carbamoylbutanoic acid; 4-(4-amino-1-oxoisoindolin-2-yl)-4-carbamoylbutanoic acid; 2-(4-amino-1-oxoisoindolin-2-yl)succinic acid; 2-(4-amino-1-oxoisoindolin-2-yl)-3-carbamoylpropanoic acid; 3-(4-amino-1-oxoisoindolin-2-yl)-3-carbamoylpropanoic acid; 2-(3-N-methylamino-1,3-dioxoisoindolin-2-yl)glutaric acid; 2-(3-N-methylamino-1,3-dioxoisoindolin-2-yl)-4-carbamoylbutanoic acid; 4-(3-N-methylamino-1,3-dioxoisoindolin-2-yl)-4-carbamoylbutanoic acid; 2-(3-N-methylamino-1,3-dioxoisoindolin-2-yl)succinic acid; 2-(3-N-methylamino-1,3-dioxoisoindolin-2-yl)-3-carbamoylpropanoic acid; 3-(3-N-methylamino-1,3-dioxoisoindolin-2-yl)-3-carbamoylpropanoic acid; 2-(3-N-methylamino-1-oxoisoindolin-2-yl)glutaric acid; 2-(3-N-methylamino-1-oxoisoindolin-2-yl)-4-carbamoylbutanoic acid; 4-(3-N-methylamino-1-oxoisoindolin-2-yl)-4-carbamoylbutanoic acid; 2-(3-N-methylamino-1-oxoisoindolin-2-yl)succinic acid; 2-(3-N-methylamino-1-oxoisoindolin-2-yl)-3-carbamoylpropanoic acid; 3-(3-N-methylamino-1-oxoisoindolin-2-yl)-3-carbamoylpropanoic acid; 2-(4-N-methylamino-1,3-dioxoisoindolin-2-yl)odipic acid; 2-(4-N-methylamino-1,3-dioxoisoindolin-2-yl)-4-carbamoylbutanoic acid; 4-(4-N-methylamino-1,3-dioxoisoindolin-2-yl)-4-carbamoylbutanoic acid; 2-(4-N-methylamino-1,3-dioxoisoindolin-2-yl)succinic acid; 2-(4-N-methylamino-1,3-dioxoisoindolin-2-yl)-3-carbamoylpropanoic acid; 3-(4-N-methylamino-1,3-dioxoisoindolin-2-yl)-3-carbamoylpropanoic acid; 2-(4-N-methylamino-1-oxoisoindolin-2-yl)glutaric acid; 2-(4-N-methylamino-1-oxoisoindolin-2-yl)-4-carbamoylbutanoic acid; 4-(4-N-methylamino-1-oxoisoindolin-2-yl)-4-carbamoylbutanoic acid; 2-(4-N-methylamino-1-oxoisoindolin-2-yl)succinic acid; 2-(4-N-methylamino-1-oxoisoindolin-2-yl)-3-carbamoylpropanoic acid; 3-(4-N-methylamino-1-oxoisoindolin-2-yl)-3-carbamoylpropanoic acid; 2-(3-methyl-1,3-dioxoisoindolin-2-yl)glutaric acid; 2-(3-methyl-1,3-dioxoisoindolin-2-yl)-4-carbamoylbutanoic acid; 4-(3-methyl-1,3-dioxoisoindolin-2-yl)-4-carbamoylbutanoic acid; 2-(3-methyl-1,3-dioxoisoindolin-2-yl)succinic acid; 2-(3-methyl-1,3-dioxoisoindolin-2-yl)-3-carbamoylpropanoic acid; 3-(3-methyl-1,3-dioxoisoindolin-2-yl)-3-carbamoylpropanoic acid; 2-(3-methyl-1-oxoisoindolin-2-yl)glutaric acid; 2-(3-methyl-1-oxoisoindolin-2-yl)-4-carbamoylbutanoic acid; 4-(3-methyl-1-oxoisoindolin-2-yl)-4-carbamoylbutanoic acid; 2-(3-methyl-1-oxoisoindolin-2-yl)succinic acid; 2-(3-methyl-1-oxoisoindolin-2-yl)-3-carbamoylpropanoic acid; 3-(3-methyl-1-oxoisoindolin-2-yl)-3-carbamoylpropanoic acid; 2-(4-methyl-1,3-dioxoisoindolin-2-yl)odipic acid; 2-(4-methyl-1,3-dioxoisoindolin-2-yl)-4-carbamoylbutanoic acid; 4-(4-methyl-1,3-dioxoisoindolin-2-yl)-4-carbamoylbutanoic acid; 2-(4-methyl-1,3-dioxoisoindolin-2-yl)succinic acid; 2-(4-methyl-1,3-dioxoisoindolin-2-yl)-3-carbamoylpropanoic acid; 3-(4-methyl-1,3-dioxoisoindolin-2-yl)-3-carbamoylpropanoic acid; 2-(4-methyl-1-oxoisoindolin-2-yl)glutaric acid; 2-(4-methyl-1-oxoisoindolin-2-yl)-4-carbamoylbutanoic acid; 4-(4-methyl-1-oxoisoindolin-2-yl)-4-carbamoylbutanoic acid; 2-(4-methyl-1-oxoisoindolin-2-yl)succinic acid; 2-(4-methyl-1-oxoisoindolin-2-yl)-3-carbamoylpropanoic acid; 3-(4-methyl-1-oxoisoindolin-2-yl)-3-carbamoylpropanoic acid; 2-(3-ethyl-1,3-dioxoisoindolin-2-yl)glutaric acid; 2-(3-ethyl-1,3-dioxoisoindolin-2-yl)-4-carbamoylbutanoic acid; 4-(3-ethyl-1,3-dioxoisoindolin-2-yl)-4-carbamoylbutanoic acid; 2-(3-ethyl-1,3-dioxoisoindolin-2-yl)succinic acid; 2-(3-ethyl-1,3-dioxoisoindolin-2-yl)-3-carbamoylpropanoic acid; 3-(3-ethyl-1,3-dioxoisoindolin-2-yl)-3-carbamoylpropanoic acid; 2-(3-ethyl-1-oxoisoindolin-2-yl)glutaric acid; 2-(3-ethyl-1-oxoisoindotin-2-yl)-4-carbamoylbutanoic acid; 4-(3-ethyl-1-oxoisoindolin-2-yl)-4-carbamoylbutanoic acid; 2-(3-ethyl-1-oxoisoindolin-2-yl)succinic acid; 2-(3-ethyl-1-oxoisoindolin-2-yl)-3-carbamoylpropanoic acid; 3-(3-ethyl-1-oxoisoindolin-2-yl)-3-carbamoylpropanoic acid; 2-(4-ethyl-1,3-dioxoisoindolin-2-yl)odipic acid; 2-(4-ethyl-1,3-dioxoisoindolin-2-yl)-4-carbamoylbutanoic acid; 4-(4-ethyl-1,3-dioxoisoindolin-2-yl)-4-carbamoylbutanoic acid; 2-(4-ethyl-1,3-dioxoisoindolin-2-yl)succinic acid; 2-(4-ethyl-1,3-dioxoisoindolin-2-yl)-3-carbamoylpropanoic acid; 3-(4-ethyl-1,3-dioxoisoindolin-2-yl)-3-carbamoylpropanoic acid; 2-(4-ethyl-1-oxoisoindolin-2-yl)glutaric acid; 2-(4-ethyl-1-oxoisoindolin-2-yl)-4-carbamoylbutanoic acid; 4-(4-ethyl-1-oxoisoindolin-2-yl)-4-carbamoylbutanoic acid; 2-(4-ethyl-1-oxoisoindolin-2-yl)succinic acid; 2-(4-ethyl-1-oxoisoindolin-2-yl)-3-carbamoylpropanoic acid; 3-(4-ethyl-1-oxoisoindolin-2-yl)-3-carbamoylpropanoic acid; 2-(3-propyl-1,3-dioxoisoindolin-2-yl)glutaric acid; 2-(3-propyl-1,3-dioxoisoindolin-2-yl)-4-carbamoylbutanoic acid; 4-(3-propyl-1,3-dioxoisoindolin-2-yl)-4-carbamoylbutanoic acid; 2-(3-propyl-1,3-dioxoisoindolin-2-yl)succinic acid; 2-(3-propyl-1,3-dioxoisoindolin-2-yl)-3-carbamoylpropanoic acid; 3-(3-propyl-1,3-dioxoisoindolin-2-yl)-3-carbamoylpropanoic acid; 2-(3-propyl-1-oxoisoindolin-2-yl)glutaric acid; 2-(3-propyl-1-oxoisoindolin-2-yl)-4-carbamoylbutanoic acid; 4-(3-propyl-1-oxoisoindolin-2-yl)-4-carbamoylbutanoic acid; 2-(3-propyl-1-oxoisoindolin-2-yl)succinic acid; 2-(3-propyl-1-oxoisoindolin-2-yl)-3-carbamoylpropanoic acid; 3-(3-propyl-1-oxoisoindolin-2-yl)-3-carbamoylpropanoic acid; 2-(4-propyl-1,3-dioxoisoindolin-2-yl)odipic acid; 2-(4-propyl-1,3-dioxoisoindolin-2-yl)-4-carbamoylbutanoic acid; 4-(4-propyl-1,3-dioxbisoindolin-2-yl)-4-carbamoylbutanoic acid; 2-(4-propyl-1,3-dioxoisoindolin-2-yl)succinic acid; 2-(4-propyl-1,3-dioxoisoindolin-2-yl)-3-carbamoylpropanoic acid; 3-(4-propyl-1,3-dioxoisoindolin-2-yl)-3-carbamoylpropanoic acid; 2-(4-propyl-1-oxoisoindolin-2-yl)glutaric acid; 2-(4-propyl-1-oxoisoindolin-2-yl)-4-carbamoylbutanoic acid; 4-(4-propyl-1-oxoisoindolin-2-yl)-4-carbamoylbutanoic acid; 2-(4-propyl-1-oxoisoindolin-2-yl)succinic acid; 2-(4-propyl-1-oxoisoindolin-2-yl)-3-carbamoylpropanoic acid; 3-(4-propyl-1-oxoisoindolin-2-yl)-3-carbamoylpropanoic acid;

2-(3-isopropyl-1,3-dioxoisoindolin-2-yl)glutaric acid; 2-(3-isopropyl-1,3-dioxoisoindolin-2-yl)-4-carbamoylbutanoic acid; 4-(3-isopropyl-1,3-dioxoisoindolin-2-yl)-4-carbamoylbutanoic acid; 2-(3-isopropyl-1,3-dioxoisoindolin-2-yl)succinic acid; 2-(3-isopropyl-1,3-dioxoisoindolin-2-yl)-3-carbamoylpropanoic acid; 3-(3-isopropyl-1,3-dioxoisoindolin-2-yl)-3-carbamoylpropanoic acid; 2-(3-isopropyl-1-oxoisoindolin-2-yl)glutaric acid; 2-(3-isopropyl-1-oxoisoindolin-2-yl)-4-carbamoylbutanoic acid; 4-(3-isopropyl-1-oxoisoindolin-2-yl)-4-carbamoylbutanoic acid; 2-(3-isopropyl-1-oxoisoindolin-2-yl)succinic acid; 2-(3-isopropyl-1-oxoisoindolin-2-yl)-3-carbamoylpropanoic acid; 3-(3-isopropyl-1-oxoisoindolin-2-yl)-3-carbamoylpropanoic acid; 2-(4-isopropyl-1,3-dioxoisoindolin-2-yl)odipic acid; 2-(4-isopropyl-1,3-dioxoisoindolin-2-yl)-4-carbamoylbutanoic acid; 4-(4-isopropyl-1,3-dioxoisoindolin-2-yl)-4-carbamoylbutanoic acid; 2-(4-isopropyl-1,3-dioxoisoindolin-2-yl)succinic acid; 2-(4-isopropyl-1,3-dioxoisoindolin-2-yl)-3-carbamoylpropanoic acid; 3-(4-isopropyl-1,3-dioxoisoindolin-2-yl)-3-carbamoylpropanoic acid; 2-(4-isopropyl-1-oxoisoindolin-2-yl)glutaric acid; 2-(4-isopropyl-1-oxoisoindolin-2-yl)-4-carbamoylbutanoic acid; 4-(4-isopropyl-1-oxoisoindolin-2-yl)-4-carbamoylbutanoic acid; 2-(4-isopropyl-1-oxoisoindolin-2-yl)succinic acid; 2-(4-isopropyl-1-oxoisoindolin-2-yl)-3-carbamoylpropanoic acid; 3-(4-isopropyl-1-oxoisoindolin-2-yl)-3-carbamoylpropanoic acid; 2-(3-butyl-1,3-dioxoisoindolin-2-yl)glutaric acid; 2-(3-butyl-1,3-dioxoisoindolin-2-yl)-4-carbamoylbutanoic acid; 4-(3-butyl-1,3-dioxoisoindolin-2-yl)-4-carbamoylbutanoic acid; 2-(3-butyl-1,3-dioxoisoindolin-2-yl)succinic acid; 2-(3-butyl-1,3-dioxoisoindolin-2-yl)-3-carbamoylpropanoic acid; 3-(3-butyl-1,3-dioxoisoindolin-2-yl)-3-carbamoylpropanoic acid; 2-(3-butyl-1-oxoisoindolin-2-yl)glutaric acid; 2-(3-butyl-1-oxoisoindolin-2-yl)-4-carbamoylbutanoic acid; 4-(3-butyl-1-oxoisoindolin-2-yl)-4-carbamoylbutanoic acid; 2-(3-butyl-1-oxoisoindolin-2-yl)

succinic acid; 2-(3-butyl-1-oxoisoindolin-2-yl)-3-carbamoylpropanoic acid; 3-(3-butyl-1-oxoisoindolin-2-yl)-3-carbamoylpropanoic acid; 2-(4-butyl-1,3-dioxoisoindolin-2-yl)odipic acid; 2-(4-butyl-1,3-dioxoisoindolin-2-yl)-4-carbamoylbutanoic acid; 4-(4-butyl-1,3-dioxoisoindolin-2-yl)-4-carbamoylbutanoic acid; 2-(4-butyl-1,3-dioxoisoindolin-2-yl)succinic acid; 2-(4-butyl-1,3-dioxoisoindolin-2-yl)-3-carbamoylpropanoic acid; 3-(4-butyl-1,3-dioxoisoindolin-2-yl)-3-carbamoylpropanoic acid; 2-(4-butyl-1-oxoisoindolin-2-yl)glutaric acid; 2-(4-butyl-1-oxoisoindolin-2-yl)-4-carbamoylbutanoic acid; 4-(4-butyl-1-oxoisoindolin-2-yl)-4-carbamoylbutanoic acid; 2-(4-butyl-1-oxoisoindolin-2-yl)succinic acid; 2-(4-butyl-1-oxoisoindolin-2-yl)-3-carbamoylpropanoic acid; and 3-(4-butyl-1-oxoisoindolin-2-yl)-3-carbamoylpropanoic acid.

These compounds can be used in cancer treatment, immunomodulating drugs, angiogenesis inhibition, and other applications listed herein. Oral dosage forms include tablets, capsules, dragees, and similar shaped, compressed pharmaceutical forms containing from 1 to 100 mg of drug per unit dosage. Isotonic saline solutions containing from 20 to 100 mg/mL can be used for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds of Formulas I and II and at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it can be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propyl hydroxybenzoates, sweetening agents and flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an immediate, sustained or delayed release of active ingredient after administration to the patient by employing procedures well known in the art.

Enzyme-linked immunosorbent assays (ELISA) for TNFα can be performed in a conventional manner. PBMC is isolated from normal donors by Ficoll-Hypaque density centrifugation. Cells are cultured in RPMI supplemented with 10% AB+ serum, 2 mM L-glutamine, 100 U/mL penicillin, and 100 mg/mL streptomycin. Drugs are dissolved in dimethylsulfoxide (Sigma Chemical) and further diluted in supplemented RPMI. The final dimethylsulfoxide concentration in the presence or absence of the drug in the PBMC suspensions is 0.25 wt %. Drugs are assayed at half-log dilutions starting at 50 mg/mL. Drugs are added to PBMC ($10^6$ cells/mL) in 96 wells plates one hour before the addition of LPS. PBMC ($10^6$ cells/mL) in the presence or absence of drug are stimulated by treatment with 1 mg/mL of LPS from *Salmonella minnesota* R595 (List Biological Labs, Campbell, Calif.). Cells are then incubated at 37° C. for 18–20 hours. Supernatants are harvested and assayed immediately for TNFα levels or kept frozen at −70° C. (for not more than 4 days) until assayed. The concentration of TNFα in the supernatant is determined by human TNFα ELISA kits (ENDOGEN, Boston, Mass.) according to the manufacturer's directions.

The following examples will serve to further typify the nature of this invention but should not be construed as a limitation in the scope thereof, which scope is defined solely by the appended claims.

EXAMPLE 1

1-(4-Nitro-1,3-dioxoisoindolin-2-yl)propane-1,3-dicarboxylic acid

To a stirred solution of glutamic acid (10 mmol) and sodium carbonate (10.5 mmol) in water (50 mL) is added ethyl 4-nitro-1,3-dioxoisoindoline-2-carboxylate (10 mmol). The resulting mixture is stirred for 3 hours. The mixture is filtered. The filtrate is then acidified to pH 1 with 4 N hydrochloric acid to afford the 1-(4-nitro-1,3-dioxoisoindolin-2-yl)propane-1,3-dicarboxylic acid.

EXAMPLE 2

1-(4-Methyl-1,3-dioxoisoindolin-2-yl)propane-1,3-dicarboxylic acid

A mixture of glutamic acid (10 mmol) and 4-methyphthalic anhydride below (10 mmol) in 20 mL of acetic acid is heated to reflux. The cooled reaction is then concentrated in vacuo. The residue is slurried in ethyl acetate and the resulting slurry filtered to afford the desired product. As an alternative to slurry filtering, column chromatography can be used to purify the desired product.

EXAMPLE 3

4-(4-Nitro-1,3-dioxoisoindolin-2-yl)-4-carbamoylbutanoic acid

A mixture of isoglutamine (20 mmol) and 3-nitrophthalic anhydride (20 mmol) in acetic acid is heated to reflux. The cooled reaction mixture is concentrated and the residue purified by chromatography to afford 2-(4-nitro-1,3-dioxoisoindolin-2-yl)-4-carbamoylbutanoic acid.

EXAMPLE 4

2-(4-Methyl-1,3-dioxoisoindolin-2-yl)-4-carbamoylbutanoic acid

A mixture of glutamine (10 mmol) and 4-methylisobenzofuran-1,3-dione (10 mmol) in 15 mL of acetic acid is heated to reflux. The cooled reaction mixture is concentrated and the residue is purified by chromatography to afford 2-(4-nitro-1,3-dioxoisoindolin-2-yl)-4-carbamoylbutanoic acid.

EXAMPLE 5

2-(4-Nitro-1,3-dioxoisoindolin-2-yl)-3-carbamoylbutanoic acid

A mixture of asparagine (10 mmol) and 3-nitrophthalic anhydride (10 mmol) in 15 ml of acetic acid is heated to reflux. The cooled reaction mixture is concentrated and the residue purified to afford 2-(4-nitro-1,3-dioxoisoindolin-2-yl)-3-carbamoylpropanoic acid.

EXAMPLE 6

2-(4-Amino-1,3-dioxoisoindolin-2-yl)-3-carbamoylpropanoic acid

A mixture of 2-(4-nitro-1,3-dioxoisoindolin-2-yl)-3-carbamoylpropanoic acid (7.5 mmol) and 10% Pd/C (200 mg) in 20 ml of dimethylformamide is treated with 60 psi of hydrogen in a Parr shaker to afford 2-(4-amino-1,3-dioxoisoindolin-2-yl)-3-carbamoylpropanoic acid.

EXAMPLE 7

2-(4-Nitro-1,3-dioxoisoindolin-2-yl)-4-carbamoylbutanoic acid

A mixture of glutamine (10 mmol) and 3-nitrophthalic anhydride (10 mmol) in 15 ml of acetic acid is heated to reflux. The cooled reaction mixture is concentrated and the residue purified by chromatography to afford 2-(4-nitro-1,3-dioxoisoindolin-2-yl)-4-carbamoylbutanoic acid.

EXAMPLE 8

2-(4-Amino-1,3-dioxoisoindolin-2-yl)-4-carbamoylbutanoic acid

A mixture of 2-(4-nitro-1,3-dioxoisoindolin-2-yl)-4-carbamoylbutanoic acid (5 mmol) and 10% Pd/C (250 mg) in dimethylformamide is hydrogenated under 60 psi of hydrogen in a Parr Type Shaker to afford 2-(4-amino-1,3-dioxoisoindolin-2-yl)-4-carbamoylbutanoic acid.

EXAMPLE 9

2-(4-Nitro-1-oxoisoindolin-2-yl)glutaric acid

To a stirred solution of glutamic acid (10 mmol) and sodium carbonate (10.5 mmol) in water (50 mL) is added 4-nitrophthalic anhydride (10 mmol). The resulting mixture is stirred for 3 hours. The mixture is filtered. The filtrate is then acidified to pH 1 with 4 N hydrochloric acid to afford 2-(4-nitro-1-oxoisoindolin-2-yl)glutaric acid.

EXAMPLE 10

2-(4-Nitro-1-oxoisoindolin-2-yl)-4-carbamoylbutanoic acid

A mixture of glutamine (10 mmol) and 4-nitrophthalic anhydride (10 mmol) in 15 mL of acetic acid is heated to reflux. The cooled reaction mixture is concentrated and the residue purified by chromatography to afford 2-(4-nitro-1-oxoisoindolin-2-yl)-4-carbamoylbutanoic acid.

EXAMPLE 11

2-(4-Nitro-1-oxoisoindolin-2-yl)succinic acid

A mixture of aspartic acid (10 mmol) and 4-nitrophthalic anhydride (10 mmol) in 20 mL of acetic acid is heated to reflux. The cooled reaction is then concentrated in vacuo. The residue is slurried in ethyl acetate and the resulting slurry filtered to afford the desired product. As an alternative to slurry filtering, simulated moving bed chromatography can be used to purify the desired product.

EXAMPLE 12

3-(4-Nitro-1-oxoisoindolin-2-yl)-3-carbamoylpropanoic acid

A mixture of isoaspargine (10 mmol) and 3-nitrophthalic anhydride (10 mmol) in 15 ml of acetic acid is heated to reflux. The cooled reaction mixture is concentrated and the residue is purified by chromatography to afford 3-(4-nitro-1-oxoisoindolin-2-yl)-3-carbamoylpropanoic acid.

EXAMPLE 13

1-(4-Nitro-1-oxoisoindolin-2-yl)propane-1,3-dicarboxylic acid dibenzyl ester

A mixture of methyl 3-nitro-2-(bromomethyl)benzoate (2.5 g, 9.12 mmol), L-glutamic acid dibenzyl ester p-toluenesulfonate salt (3.0 g, 9.12 mmol) and triethylamine (2.0 g, 20.0 mmol) in THF (50 mL) is heated at reflux for 16 hours. The mixture is diluted with methylene chloride (150 mL) and washed with water (2×40 mL), brine (40 mL), dried and concentrated to an oil. The oil is purified by chromatography (silica gel, Hexane:ethoxyacetic acid 7:3) to give 1-(4-nitro-1-oxoisoindolin-2-yl)propane-1,3-dicarboxylic acid dibenzyl ester (2.65 g, 59%); $^1$H NMR (CDCl$_3$) δ8.39 (d, J=7.8 Hz, 1H), 8.16 (d, J=7.3 Hz, 1H), 7.69 (t, J=7.9 Hz, 1H), 7.30 (m, 10H), 5.29 (s, 2H), 5.29–5.13 (m, 1H), 5.03 (s, 2H), 4.98 (d, J=19.1 Hz, 1H), 4.85 (d, J=19.2 Hz, 1H), 2.54–2.39 (m, 4H); $^{13}$C NMR (CDCl$_3$) δ171.79, 169.92, 166.72, 143.47, 137.25, 135.49, 135.04, 134.99, 130.17, 129.67, 128.62, 128.52, 128.29, 128.25, 128.23, 127.04, 67.49, 66.58, 53.70, 48.35, 30.87, 24.79.

EXAMPLE 14

1-(4-Amino-1-oxoisoindolin-2-yl)propane-1,3-dicarboxylic acid

A mixture of 1-(4-nitro-1-oxoisoindolin-2-yl)propane-1,3-dicarboxylic acid dibenzyl ester (2.6 g, 5.3 mmol), 10%Pd/C (0.26 g) and methanol (50 mL) is hydrogenated at 50 psi of hydrogen for 6 hours. The mixture is filtered through celite and the celite pad is washed with methanol (50 mL). The filtrate is concentrated in vacuo to give 1-(4-amino-1-oxoisoindolin-2-yl)propane-1,3-dicarboxylic acid (1.2 g, 81%); mp 183–185° C.; $^1$H NMR (DMSO-d$_6$) δ7.17 (t, J=7.6 Hz, 1H), 6.89 (d, J=7.3 Hz, 1H), 6.79 (d, J=7.8 Hz, 1H), 5.50 (b, 2H), 4.82–4.77 (m, 1H), 4.23 (s, 2H), 2.31–1.98 (m, 4H); $^{13}$C NMR (DMSO-d$_6$) δ173.46, 172.28, 168.98, 143.58, 132.21, 128.73, 125.65, 116.24, 110.34, 52.83, 45.19, 30.32, 24.42; Anal. Calcd. For C$_{13}$H$_{14}$N$_2$O$_5$; C, 56.11; H, 5.07; N, 10.07. Found: C, 55.95; H, 5.37; N, 9.73.

EXAMPLE 15

1-(4-Nitro-1,3-dioxoisoindolin-2-yl)propane-1,3-dicarboxylic acid

A mixture of 3-nitrophthalic anhydride (1.5 g, 7.77 mmol) and L-glutamic acid (1.2 g, 7.77 mmol) in DMF (15 mL) is heated at 85° C. for 6 hours. The mixture is concentrated in vacuo and the residue is purified by chromatography (silica gel, CH$_2$Cl$_2$:CH$_3$OH 95:5) to give 1-(4-nitro-1,3-dioxoisoindolin-2-yl)propane-1,3-dicarboxylic acid (1.51 g, 60%); $^1$H NMR (DMSO-d$_6$) δ8.32 (d, J=7.9 Hz, 1H), 8.21 (d, J=7.3 Hz, 1H), 8.10 (t, J=7.8 Hz, 1H), 4.88–4.82 (dd, J=3.0 and 10.0 Hz, 1H), 2.35–2.20 (m, 4H).

EXAMPLE 16

1-(4-Amino-1,3-dioxoisoindolin-2-yl)propane-1,3-dicarboxylic acid

A mixture of 1-(4-nitro-1,3-dioxoisoindolin-2-yl) propane-1,3-dicarboxylic acid (1.4 g, 4.34 mmol) and 10%Pd/C (0.14 g) in methanol (50 mL) is hydrogenated at 50 psi of hydrogen for 2 hours. The mixture is filtered through celite and the celite pad is washed with methanol (40 mL). The filtrate is concentrated and the residue is slurried with ethyl acetate (25 mL) and hexane (20 mL) to give 1-(4-amino-1,3-dioxoixoindolin-2-yl)propane-1,3-dicarboxylic acid (1.02 g, 80%); mp 198–200° C.; $^1$H NMR (DMSO-$d_6$) δ7.46 (t, J=7.6 Hz, 1H), 7.02–6.97 (m, 2H), 6.49 (s, 2H), 4.72–4.68 (m, 1H), 2.38–2.20 (m, 4H); $^{13}$C NMR (DMSO-$d_6$) δ173.60, 170.60, 168.90, 167.64, 146.64, 135.33, 132.03, 121.56, 110.89, 108.68, 50.56, 30.39, 23.76; Anal. Calcd. For $C_{13}H_{12}N_2O_6$: C, 53.43; H, 4.14; N, 9.59. Found: C, 53.37; H, 4.41; N, 9.43.

EXAMPLE 17

2-(4-Nitro-1,3-dioxoisoindolin-2-yl)-4-carbamoylbutanoic acid (40761-10)

A mixture of 3-nitrophthalic anhydride (1.5 g, 7.8 mmol) and L-glutamine (1.14 g, 7.8 mmol) in DMF (15 mL) is heated at 85–90° C. for 4 hours. The mixture is concentrated in vacuo and the residue is slurried with water (30 mL). The resulting slurry is filtered and the solid is washed with water (10 mL), dried (60° C., <1 mm Hg) to give 2-(4-nitro-1,3-dioxoisoindolin-2-yl)-4-carbamoylbutanoic acid (1.82 g, 73%); mp 182–184° C.; $^1$H NMR (DMSO-$d_6$) δ8.33 (d, J=7.7 Hz, 1H), 8.22 (d, J=7.0 Hz, 1H), 8.11 (t, J=7.8 Hz, 1H), 7.19 (s, 1H), 6.73 (s, 1H), 4.82–4.77 (dd, J=4.6 and 9.8 Hz, 1H), 2.36–2.11 (m, 4H); $^{13}$C NMR (DMSO-$d_6$) δ173.21, 170.03, 165.43, 162.75, 144.45, 136.70, 132.98, 128.83, 127.25, 122.52, 51.87, 31.31, 23.87; Anal. Calcd. For $C_{13}H_{11}N_3O_7$: C, 48.60; H, 3.45; N, 13.08. Found: C, 48.52; H, 3.28; N, 13.05.

EXAMPLE 18

2-(4-Amino-1,3-dioxoisoindolin-2-yl)-4-carbamoylbutanoic acid (40761-18)

A mixture of 2-(4-nitro-1,3-dioxoisoindolin-2-yl)-4-carbamoylbutanoic acid (1.75 g, 5.45 mmol) and 10% Pd/C (0.2 g) in methanol (52 mL) is hydrogenated at 50 psi of hydrogen for 2 hours. The mixture is filtered through celite and the celite pad is washed with methanol (30 mL). The filtrate is concentrated in vacuo and the residue is slurried with ethyl acetate (20 mL) for 30 min. The resulting slurry is filtered and the solid is washed with ethyl acetate (10 mL) and dried (60° C., <1 mmHg) to give 2-(4-amino-1,3-dioxoisoindolin-2-yl)-4-carbamoylbutanoic acid (1.39 g, 88%) as a yellow solid; mp 165–167° C.; $^1$H NMR (DMSO-$d_6$) δ13.08 (b, 1H), 7.46 (t, J=7.8 Hz, 1H), 7.22 (s, 1H), 7.02–6.97 (dd, J=4.1 and 5.5 Hz, 1H), 6.73 (s, 1H), 6.51 (s, 2H), 4.68–4.62 (dd, J=4.5 and 10.5 Hz, 1H), 2.50–1.99 (m, 4H); $^{13}$C NMR (DMSO-$d_6$) δ173.07, 170.75, 168.88, 167.63, 146.66, 135.36, 132.03, 121.58. 110.87, 108.63, 50.74, 31.34, 24.03; Anal. Calcd. For $C_{13}H_{13}N_3O_5$: C, 53.60; H, 4.50; N, 14.43. Found: C, 53.71; H, 4.40; N, 14.31.

EXAMPLE 19

Tablets, each containing 50 mg of 1-(4-nitro-1,3-dioxoisoindolin-2-yl)propane-1,3-dicarboxylic acid, can be prepared in the following manner:

| Constituents (for 1,000 tablets) | |
|---|---|
| 1-(4-nitro-1,3-dioxoisoindolin-2-yl) propane-1,3-dicarboxylic acid | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 20

Gelatin dry-filled capsules, each containing 100 mg of 2-(4-nitro-1,3-dioxoisoindolin-2-yl)-4-carbamoylbutanoic acid, can be prepared in the following manner:

| Composition (for 1,000 capsules | |
|---|---|
| 2-(4-nitro-1,3-dioxoisoindolin-2-yl)-4-carbamoyl butanoic acid | 100.0 g |
| microcrystalline cellulose | 30.0 g |
| sodium lauryl sulfate | 2.0 g |
| magnesium stearate | 8.0 g |

The sodium lauryl sulfate is sieved into the 2-(4-nitro-1,3-dioxoisoindolin-2-yl)-4-carbamoylbutanoic acid through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

EXAMPLE 21

A 0.2% injection solution can be prepared, for example, in the following manner:

| 2-(4-nitro-1,3-dioxoisoindolin-2-yl)-4-carbamoylbutanoic acid | 5.0 g |
|---|---|
| sodium chloride | 22.5 g |
| phosphate buffer pH 7.4 | 300.0 g |
| demineralized water to | 2500.0 mL |

2-(4-Nitro-1,3-dioxoisoindolin-2-yl)-4-carbamoylbutanoic acid is dissolved in 1,000 mL of water and filtered through a microfilter. The buffer solution is added and the whole is made up to 2,500 mL with water. To prepare dosage unit forms, portions of 1.0 or 2.5 mL each are introduced into glass ampoules (each containing respectively 2.0 or 5.0 mg of imide).

What is claimed is:

1. A compound selected from the group consisting of a 1,3-dioxoisoindoline of the formula:

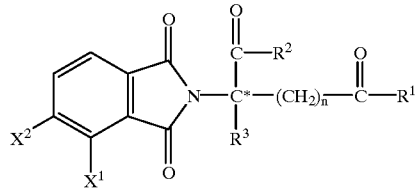

in which:
one of $X^1$ and $X^2$ is nitro, or NH—Z, and the other of $X^1$ or $X^2$ is hydrogen;
each of $R^1$ and $R^2$ independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and,
n has a value of 0, 1, or 2;
provided that if one of $X^1$ and $X^2$ is nitro, and n is 1 or 2, then $R^1$ and $R^2$ are other than hydroxy; and
if —$COR^1$ and —$(CH_2)_nCOR^2$ are different, the carbon atom designated C* constitutes a center of chirality; and,
the salts thereof.

2. A compound according to claim 1 in which $R^1$ is hydroxy, $R^2$ is amino, $R^3$ is hydrogen, and n is 1 or 2.

3. A compound according to claim 1 in which $R^1$ is amino, $R^2$ is hydroxy, $R^3$ is hydrogen, and n is 1 or 2.

4. The compound according to claim 1 in which the 1,3-dioxo-isoindoline is 1-(4-nitro-1,3-dioxoisoindolin-2-yl)propane-1,3-dicarboxylic acid; 4-(4-nitro-1,3-dioxoisoindolin-2-yl)-4-carbamoylbutanoic acid; 2-(4-nitro-1,3-dioxoisoindolin-2-yl)-3-carbamoylbutanoic acid; 2-(4-amino-1,3-dioxoisoindolin-2-yl)-3-carbamoylpropanoic acid; 2-(4-amino-1,3-dioxoisoindolin-2-yl)-3-carbamoylpropanoic acid; 2-(4-nitro-1,3-dioxoisoindolin-2-yl)-4-carbamoylbutanoic acid, or 2-(4-amino-1,3-dioxoisoindolin-2-yl)-4-carbamoylbutanoic acid.

5. A method of reducing or inhibiting undesirable levels of TNFα in a mammal which comprises administering thereto an effective amount of a compound as recited in claim 1.

6. A method of treating in a mammal a disease selected from the group consisting of, arthritis, rheumatoid arthritis, osteoarthritis, reperfusion injury, inflammatory bowel disease, Crohn's disease, ulcerative colitis, systemic lupus erythrematosis, scleroderma, aphthous ulcers, graft versus host disease, asthma, chronic obstructive respiratory disease, adult respiratory distress syndrome, sarcoidosis, psoriasis, stopic dermatitis, endotoxemia and toxic shock syndrome, malaria, leprosy, cachexia, and acquired immune deficiency syndrome comprising administering a compound according to claim 1 to a patient in need thereof.

7. A method of treating a cancerous condition in a mammal, which condition is sensitive to a compound recited in claim 1, comprising administering to the mammal, an effective amount of said compound.

8. A method of treating angiogenesis, in a mammal, which condition is sensitive to a compound recited in claim 1, comprising administering to the mammal, an effective amount of said compound.

9. A pharmaceutical composition comprising a quantity of a compound according to claim 1 sufficient upon administration in a single or multiple dose regimen to reduce levels of TNFα in a mammal in combination with a pharmaceutically acceptable carrier.

10. A compound selected from the group consisting of a 1,3-dioxoisoindoline of the formula:

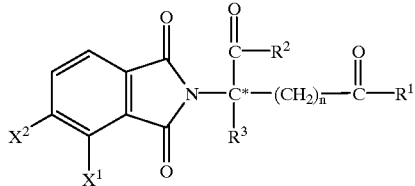

in which:
one of $X^1$ and $X^2$ is alkyl of one to six carbons;
each of $R^1$ and $R^2$ independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2; and,
if —$COR^1$ and —$(CH_2)_nCOR^2$ are different, the carbon atom designated C* constitutes a center of chirality; and,
the salts thereof.

11. A compound according to claim 8 in which $R^1$ is hydroxy, $R^2$ is amino, $R^3$ is hydrogen, and n is 1 or 2.

12. A compound according to claim 8 in which $R^1$ is amino, $R^2$ is hydroxy, $R^3$ is hydrogen, and n is 1 or 2.

13. The compound according to claim 8 in which the 1,3-dioxo-isoindoline is 1-(4-methyl-1,3-dioxoisoindolin-2-yl)propane-1,3-dicarboxylic acid; 2-(4-methyl-1,3-dioxoisoindolin-2-yl)-4-carbamoylbutanoic acid.

14. A method of reducing or inhibiting undesirable levels of TNFα in a mammal which comprises administering thereto an effective amount of an a compound as recited in claim 10.

15. A method of treating in a mammal a disease selected from the group consisting of, arthritis, rheumatoid arthritis, osteoarthritis, reperfusion injury, inflammatory bowel disease, Crohn's disease, ulcerative colitis, systemic lupus erythrematosis, scleroderma, aphthous ulcers, graft versus host disease, asthma, chronic obstructive respiratory disease, adult respiratory distress syndrome, sarcoidosis, psoriasis, stopic dermatitis, endotoxemia and toxic shock syndrome, malaria, leprosy, cachexia, and acquired immune deficiency syndrome comprising administering a compound according to claim 10 to a patient in need thereof.

16. A method of treating a cancerous condition in a mammal, which condition is sensitive to a compound recited in claim 10, comprising administering to the mammal, an effective amount of said compound.

17. A method of treating angiogenesis, in a mammal, which condition is sensitive to a compound recited in claim 10, comprising administering to the mammal, an effective amount of said compound.

18. A pharmaceutical composition comprising a quantity of a compound according to claim 10 sufficient upon administration in a single or multiple dose regimen to reduce levels of TNFα in a mammal in combination with a pharmaceutically acceptable carrier.

* * * * *